US011597909B2

(12) United States Patent
Weber et al.

(10) Patent No.: US 11,597,909 B2
(45) Date of Patent: Mar. 7, 2023

(54) METHOD FOR THE FORMATION OF RENAL TUBULES (71) Applicant: LEIBNIZ-INSTITUT FÜR POLYMER-FORSCHUNG DRESDEN E.V., Dresden (DE)

(72) Inventors: Heather Weber, Dresden (DE); Mikhail Tsurkan, Dresden (DE); Valentina Magno, Dresden (DE); Uwe Freudenberg, Dresden (DE); Carsten Werner, Dresden (DE)

(73) Assignee: LEIBNIZ-INSTITUT FÜR POLYMER-FORSCHUNG DRESDEN E.V., Dresden (DE)

( * ) Notice: Subject to any disclaimer, the term of this patent is extended or adjusted under 35 U.S.C. 154(b) by 247 days.

(21) Appl. No.: 16/301,956

(22) PCT Filed: May 12, 2017

(86) PCT No.: PCT/DE2017/100407
§ 371 (c)(1),
(2) Date: Nov. 15, 2018

(87) PCT Pub. No.: WO2017/198257
PCT Pub. Date: Nov. 23, 2017

(65) Prior Publication Data
US 2019/0241866 A1   Aug. 8, 2019

(30) Foreign Application Priority Data
May 17, 2016 (DE) ............ 10 2016 109 067.0

(51) Int. Cl.
C12N 5/00 (2006.01)
C12N 5/071 (2010.01)
C12M 3/00 (2006.01)
G01N 33/50 (2006.01)
C12N 11/04 (2006.01)
C12N 5/0775 (2010.01)
C12M 1/32 (2006.01)
C12N 5/074 (2010.01)

(52) U.S. Cl.
CPC ........... *C12N 5/0062* (2013.01); *C12M 21/08* (2013.01); *C12M 23/12* (2013.01); *C12N 5/0663* (2013.01); *C12N 5/0668* (2013.01); *C12N 5/0686* (2013.01); *C12N 5/0687* (2013.01); *C12N 5/0696* (2013.01); *C12N 11/04* (2013.01); *G01N 33/5088* (2013.01); *C12N 2500/50* (2013.01); *C12N 2501/734* (2013.01); *C12N 2501/91* (2013.01); *C12N 2502/25* (2013.01); *C12N 2502/256* (2013.01); *C12N 2502/28* (2013.01); *C12N 2510/04* (2013.01); *C12N 2513/00* (2013.01); *C12N 2533/30* (2013.01)

(58) Field of Classification Search
CPC .. C12N 5/0062; C12N 5/0668; C12N 5/0686; C12N 5/0663; C12N 5/0696; C12N 2502/256; C12N 2510/04; C12N 2502/28; C12N 2533/30; C12N 2501/91; C12N 2513/00; C12M 21/08
See application file for complete search history.

(56) References Cited

U.S. PATENT DOCUMENTS

| 8,568,771 B2 | 10/2013 | Cantaluppi et al. | |
|---|---|---|---|
| 2012/0058943 A1* | 3/2012 | Werner | ............... A61L 27/52 |
| | | | 514/8.1 |
| 2013/0190210 A1* | 7/2013 | Murphy | ............... A61L 27/34 |
| | | | 506/14 |
| 2015/0246132 A1 | 9/2015 | Freudenberg | |
| 2016/0369230 A1 | 12/2016 | Freudenberg | |

FOREIGN PATENT DOCUMENTS

| EP | 2 078 073 B1 | 7/2009 | |
|---|---|---|---|
| JP | 2011502142 | 1/2011 | |
| WO | WO 2015/069192 A1 | 5/2015 | |
| WO | WO2016179242 A1 * | 11/2016 | ............ A61L 27/38 |
| WO | WO-2016179242 A1 * | 11/2016 | ............ A61L 27/18 |

OTHER PUBLICATIONS

DesRochers et al. Tissue-Engineered Kidney Disease Models. Adv Drug Deliv Rev. Apr. 20, 2014; 0: 67-80 (Year: 2014).*
Jang et al. Human kidney proximal tubule-on-a-chip for drug transport and nephrotoxicity assessment. Integr. Biol., 2013, 5, 1119-1129 (Year: 2013).*
Lau et al. Bioresponsive hydrogel scaffolding systems for 3D constructions in tissue engineering and regenerative medicine. Nanomedicine (2013) 8(4), 655-668 (Year: 2013).*
Humes et al. Tubulogenesis from isolated single cells of adult mammalian kidney: clonal analysis with a recombinant retrovirus. Am. J. Physiol. 271 (Renal Fluid Electrolyte Physiol. 40): F42-F49 (Year: 1996).*
Chung et al. Bioadhesive hydrogel microenvironments to modulate epithelial morphogenesis. Biomaterials 29 (2008) 2637-2645 (Year: 2008).*
International Search Report issued by the European Patent Office in International Application PCT/DE2017/100407.
Mollet, B. et al. "A modular approach to easily processable supramolecular bilayered scaffolds with tailorable properties", J. Mater Chem. B., 2014, p. 2483-2493.
Thompson, M. et al. "Self-Assembling Hydrogels Crosslinked Solely by Receptor-Ligand Interactions: Tunability, Rationalization of Physical Properties, and 3D Cell Culture", Chemistry—A European Journal, 2015, 21 (8), p. 3178-3182.

(Continued)

Primary Examiner — Taeyoon Kim
(74) Attorney, Agent, or Firm — Ursula B. Day (57) ABSTRACT The invention relates to a method for the formation of renal tubules by embedding individual renal cells into a synthetic hydrogel, which is based on polyethylene glycol as a component, and the culturing of the cells until tubule structures are formed. The culturing can be continued until the obtained tubule structures correspond in terms of size, structure, morphology and functionality to adult human renal tubules or are at least similar thereto.

8 Claims, 9 Drawing Sheets

(56) References Cited

OTHER PUBLICATIONS

Tsurkan, M. et al. "Growth factor delivery from hydrogel particle aggregates to promote tubular regeneration after acute kidney injury", Journal of Controlled release 167, 2013, p. 248-255.

Astashkina, A. I. et al.: "Comparing predictive drug nephrotoxicity biomarkers inkidney 3-D primary organoid culture and immortalized cell lines", Biomaterials, elsevier science publishers, Barking, GB, 33 (18), 2012, p. 4712-4721.

Masaaki, Miya et al. "Enhancement of in vitro human tubulogenesis by endothelial cell-derived factors: implications for in vivo tubular regeneration after injury", American Journal of Physiology—Renal Physiology, 2011, p. 387-395.

Balajikarthick Subramanian et al.: "Tissue-Engineered Three-Dimensional In Vitro Models for Normal and Diseased Kidney", Tissue Engineering Part A, 16 (9), 2010, p. 2821-2831.

Tsurkan M. et al. Defined Polymer-Peptide Conjugates to Form Cell-Instructive starPEG-Heparin Matrices in Situ, Advanced Materials, 25 (18), 2013, p. 2606-2610.

Astashkina, A. I. et al. A 3-D organoid kidney culture model engineered for high-throughput nephrotoxicity assays. Biomaterials 2012.

Desrochers, T. et al. "Bioengineered 3D Human Kidney Tissue, a Platform for the Determination of Nephrotoxicity", Plos One, 8 (3), 2013, p. e59219.

Desrochers, T. et al.: „Tissue engineered kidney disease models, Advanced drug delivery reviews, vol. 69, 2013, p. 67-80.

Weber, H. et al. "Heparin-based hydrogels induce human renal tubulogenesis in vitro", acta biomaterialia, Elsevier, 57, 2017, p. 59-69.

Archibald, K. et al. Open letter to Prime Minister Cameron and Health Secretary Andrew Lansley on Safety of Medicines. Lancet, 2011: p. 1915.

Davies J., Engineered Renal Tissue as a potential platform for pharmacokinetic and nephrotoxicity testing. Drug Discovery Today (2014).

Masaaki Miya et al. "Enhancement of in vitro human tubulogenesis by endothelial cell-derived factors: implications for in vivo tubular regeneration after injury", Am J Physiol Renal Physiol, 2011, vol. 301, p. F387-F395.

Heather Weber et al. "3D renal organoid model for nephrotoxicity applications", regenerative medicine, 2015, vol. 10, No. 7, suppl., p. 202, No. pp. 121.

* cited by examiner

# METHOD FOR THE FORMATION OF RENAL TUBULES

CROSS-REFERENCES TO RELATED APPLICATIONS

This application is the U.S. National Stage of International Application No. PCT/DE2017/100407, filed May 12, 2017, which designated the United States and has been published as International Publication No. WO 2017/198257 A1 and which claims the priority of German Patent Application, Serial No. 10 2016 109 067.0 filed May 17, 2016, pursuant to 35 U.S.C. 119(a)-(d) the description of which is hereby incorporated by reference.

BACKGROUND OF THE INVENTION

The invention relates to a method for the formation of renal tubules and thus for establishing an ex vivo model for renal tubules (renal tubules), with which development processes can be studied and drug toxicity tests can be performed.

The nephrons are a functional subunit of the kidney composed of renal corpuscles and renal tubules. The renal tubules, especially the proximal tubules, play an important role in the excretion of metabolic products (toxins) and the reabsorption of nutrients from the urine. Accordingly, the proximal tubules react very sensitively to metabolic products and drugs excreted via the kidney.

Currently used nephrotoxicity assays are based on either two-dimensional in vitro cultures or animal models. However, the 2D culture of cells is very artificial due to the lack of cell-cell and cell-matrix contact and thus far removed from the physiologically relevant environment. For this reason, kidney toxicity studies are mostly carried out in animal models. However, these studies show in about 50% of cases contradictory trends compared to the human response to drugs, such as disclosed, for example, in the publication Archibald K, Coleman R, Foster C. Open letter to Prime Minister David Cameron and Health Secretary Andrew Lansley on safety of medicines. Lancet. 2011; 377: 1915.

For this reason, kidney-specific organoid assays have been developed to replace the widely used renal toxicity assays, as described by Davies J., Engineered Renal Tissue as a potential platform for pharmacokinetic and nephrotoxicity testing. Drug Discovery Today (2014). It was shown here that 3D organoid models are better suited to reconstruct the nephrotoxic effects in vivo compared to the conventional use of immortalized cell lines (2D culture) (Astashkina A. I. et al., Comparing predictive drug nephrotoxicity biomarkers in kidney 3-D primary organoid culture and immortalized cell lines. Biomaterials (2012) 33 4712-21).

In addition, a renal tubular model based at least partially on synthetic materials known, inter alia, from the document Astashkina A. I. et al. A 3-D organoid kidney culture model engineered for high-throughput nephrotoxicity assays. Biomaterials (2012), which uses hyaluronic acid (HA) and polyethylene glycol diacrylates (PEGDA), and a tubular model based on a porous hydrogels of silk proteins filled with a mixture of collagen and Matrigel™. The model based on porous hydrogel utilized healthy or disease-specific modified embryonic murine renal epithelial cells. The model based on HA-PEGDA showed promising results with high-throughput-compatible assays. Overall, the 3D studies have provided evidence for the relevance of 3D cell culture models in the context of kidneys.

Furthermore, renal 3D tubule models based on collagen, Matrigel™ or combinations of both biopolymer preparations were developed, as described, inter alia, in DesRochers, T. M., Suter, L., Roth, A., Kaplan, D. Bioengineered 3D Human Kidney Tissue, a Platform for the Determination of Nephrotoxicity. Plos One 8, (2013).

The previously described organoid models according to the prior art have the following disadvantages, in addition to the abovementioned restrictions with respect to the artificial 2D environment in a conventional cell culture or the animal models, which are in some cases not very meaningful or even contrary due to large biological differences:

The organoid models use cells of animal origin as well as embryonic or induced pluripotent stem cells, which are of limited use due to species differences, for ethical reasons, and due to the danger of the formation of a teratoma. In addition, the used biopolymer-based matrix systems have strong batch-dependent fluctuations and are therefore difficult to apply reproducibly. In addition, no defined variation in the mechanical and biomolecular properties and hence also no study of these parameters for tubulogenesis are possible.

Biologically, it is also disadvantageous that the dimensions, shape and morphology of the tubules-like structures are clearly different from those of the desired human renal tubules.

In particular, the HA-PEGDA hydrogel also utilizes fragments of proximal tubules derived from mouse kidneys and is therefore not suitable for describing the human situation or studying the process of human tubulogenesis.

The object of the invention was to produce a defined three-dimensional model system of human tubules with modulatable properties, which has a structure and function that is very similar to the model of the human proximal renal tubules and allows the formation of tubules and/or to examine their response to drugs.

SUMMARY OF THE INVENTION

The model system should be robust and have long-term stability to allow reproducible studies over longer periods of time, i.e. at least 4-6 weeks. In addition, the effect of different cell-signaling signals, such as mechanical properties, convertibility, presentation of soluble signaling molecules, the natural cell environment, the so-called extracellular matrix, on the tubulogenesis and the drug effect should also be characterizable by using meaningful assays, for example, with respect to metabolic activity and toxicity and renal disease markers, as well as extended single cell analyzes, for example regarding the morphology, immunochemistry, flow cytometry, PCR, Western Blot. The response to the administration of active ingredients and drugs should be broadly comparable to that of established in vivo tests, thereby helping to limit costly and ethically questionable animal experiments.

In addition, array techniques should allow up-scaling of broadband screening.

The object of the invention is achieved by a method having the features of the following paragraphs. Further developments are recited in the dependent claims.

In the method according to the invention for the formation of kidney tubules, individual kidney cells are embedded in a synthetic hydrogel based on polyethylene glycol (PEG) as a component, and the cells are cultivated until tubule structures are formed.

According to a particularly advantageous embodiment, the PEG hydrogel system is crosslinked via enzymatically cleavable peptides, preferably by matrix metalloproteinase-cleavable peptides (MMP peptides), whereby the hydrogel system is cleavable and locally convertible.

In this case, the polyethylene glycol molecules can be crosslinked by the conjugated peptides to a PEG-peptide/PEG system and thus form PEG-peptide/PEG hydrogels. Preferred are PEG-MMP/PEG hydrogels. Preferably, a multi-armed polyethylene glycol is used as the polyethylene glycol. Preference is given to the four-armed polyethylene glycol (star PEG).

According to a further preferred embodiment of the invention, the PEG molecules can be crosslinked with one another by the peptide molecules with molecules of a glycosaminoglycan, for example heparin, and form hydrogels. Preferably, PEG-MMP/heparin hydrogel systems are used in this embodiment, wherein star-PEG-MMP/heparin hydrogel systems have proven to be particularly advantageous. In one embodiment, the hydrogel matrix of the hydrogel is formed by covalent cross-linking of a thiol-terminated star-PEG-peptide conjugate and a heparin functionalized by maleimide, preferably by 4-6 maleimide groups. The hydrogel matrix is crosslinked via a Michael addition.

The kidney cells used for the culture are preferably derived from renal tubule cell lines or are primary renal tubule cells or cells derived from induced pluripotent stem cells (iPSCs) or from mesenchymal stem cells.

It is particularly advantageous if the kidney cells are derived from human renal tubule cell lines or are human primary renal tubule cells or are cells derived from human induced pluripotent stem cells (iPSCs) or from human mesenchymal stem cells.

The renal tubule cells may be, for example, proximal tubule cells, distal tubule cells or collecting tubule cells. The primary renal tubule cells are preferably human primary proximal renal tubule cells.

Advantageously, the renal tubule cell line is an immortalized proximal tubular epithelial cell line derived from normal adult human kidney tissue.

Cultivation is preferably continued until the size, structure and morphology and functionality of the tubule structures match or at least resemble adult human renal tubules.

The functionality of kidney tubules can be described, for example, by the expression of human renal markers, preferably polarization markers, the responsiveness to known nephrotoxic compounds, for example cisplatin, and the resulting expression of renal injury markers, for example the renal injury marker KIM1, and apoptosis markers, for example cleaved caspase-3, and in that the tubules are capable of transporting anionic charged organic molecules into the lumen of the tubules.

According to one embodiment of the invention, tubule cells are co-cultivated together with mesenchymal stem cells, kidney cells or endothelial cells which are present in the hydrogel co-localized with the tubule cells.

Particularly preferred is a co-cultivation of the tubule cells together with human mesenchymal stem cells and/or human kidney cells and/or human endothelial cells, which are present in the hydrogel co-localized with the tubule cells.

The procedure can be carried out with and without serum, i.e. 0% (v/v) serum.

With the method, human kidney tubules can be generated in a three-dimensional hydrogel matrix, with a size, structure, and morphology and function that match or are at least similar to adult human renal tubules.

The method can be used for three-dimensional monitoring of the formation of human renal tubules or of renal tubules of mammals, for example of mice or rats.

Particularly advantageous is here the use for characterizing the effects of the hydrogel stiffness and/or the effects of the degradation of the hydrogel via enzymatically cleavable peptide bridges, preferably MMP, and/or the characterization of the effects of the presence of tubules, such as heparin, and/or of peptides, preferably signaling peptides derived from proteins of the extracellular matrix (ECM), on the formation of kidney tubules by incorporation of glycosaminoglycans and/or peptides in the synthetic hydrogel.

The method for characterizing the effects of soluble molecules or active substances, such as signaling molecules, in particular growth factors, can be applied to the formation of the renal tubules by adding a compound to the culture medium or by embedding the component in the hydrogel.

Particularly preferred is the application of the method for analyzing the toxicity of a compound to renal tubules by adding this compound to the medium or embedding this compound in the hydrogel.

The studies of tubulogenesis or nephrotoxicity may advantageously be carried out by performing the method of a 24-, 48- or 96-well plate.

BRIEF DESCRIPTION OF THE DRAWING

Further details, features and advantages of embodiments of the invention will become apparent from the following description of exemplary embodiments with reference to the accompanying drawings, which show in.

DETAILED DESCRIPTION OF PREFERRED EMBODIMENTS

Figure 1:
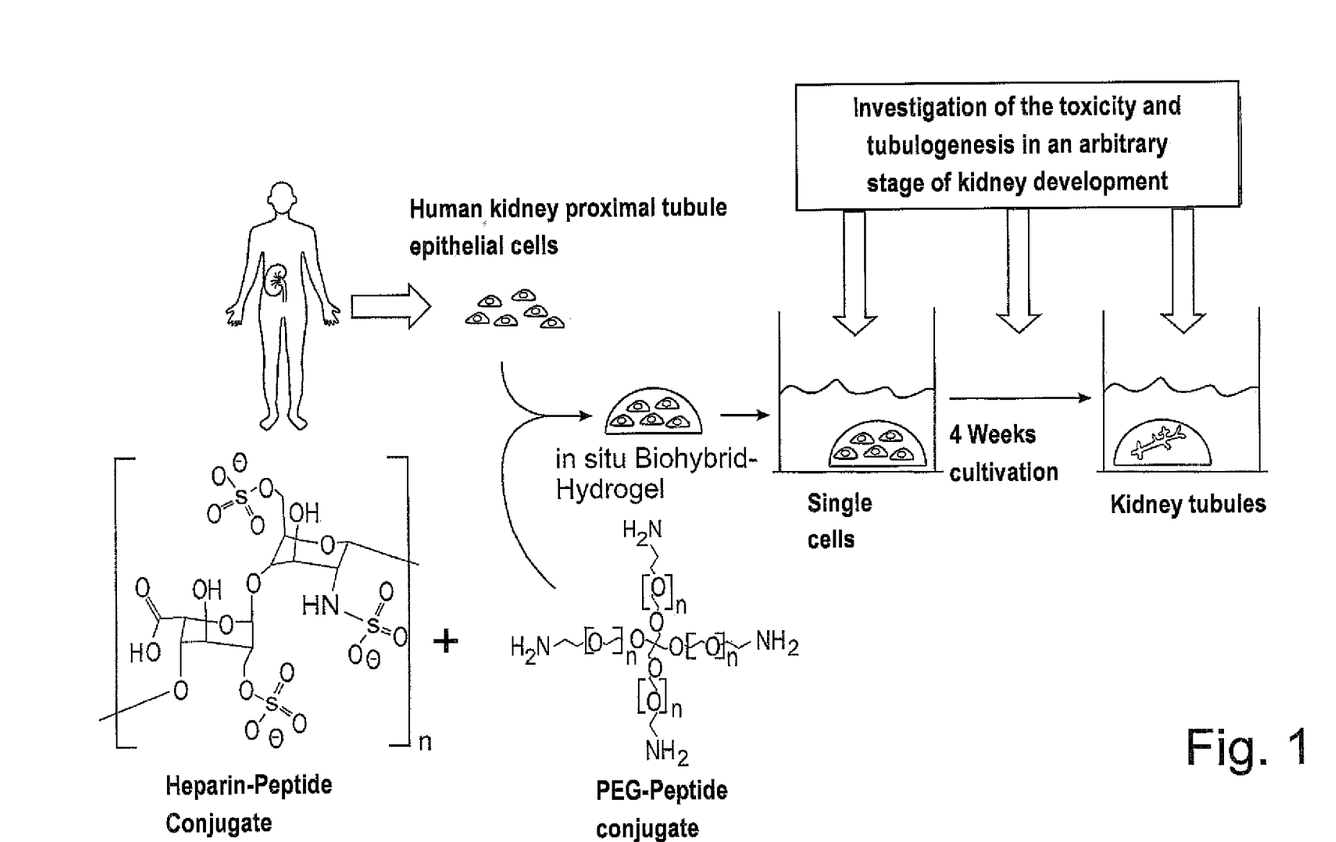
FIG. 1: the experimental setup of an ex vivo renal tubule assay.

The method shown in FIG. 1 is based on the use of hydrogels formed from cross-linked four-armed polyethylene glycol (Stern-PEG) and heparin functionalized with multiple maleimide groups. The formation of such hydrogels has already been described, for example, in Tsurkan M. V. et al. Defined Polymer Peptides Conjugates to Form Cell-Instructive StarPEG-Heparin Matrices In Situ. Advanced Materials (2013). Star-PEG was modified to include a peptide cleavable by matrix metalloproteinase (MMP) to allow for a cell-controlled local degradation and reconfiguration of the hydrogel matrix. Heparin-maleimide and star PEG-are both dissolved in a phosphate-buffered saline solution (PBS). By mixing the two solutions, a hydrogel forms in less than a minute by a Michael-type addition between heparin-maleimide and the thiol-terminated PEG-peptide conjugates or the thiol-terminated PEG. Human proximal tubule epithelial cells were already embedded in the hydrogel by initial admixing to the heparin-maleimide solution using a pipette followed by mixing the heparin-maleimide cell mixture with the star-PEG solution.

Human kidney tubule epithelial cells of the cell line HK-2 (ATCC CRL-2190) were cultured in DMEM/F-12 medium of the company Gibco, supplemented with 10% fetal bovine serum (FBS) from the company Biochrom) and 1% penicillin/streptomycin solution. The HK-2 cells were embedded in the hydrogels, 50,000 cells per hydrogel, and cultured for four weeks. The medium was changed every three days. The formation of tubules occurred after about three weeks.

FIG. 1 shows, schematically, a heparin-peptide conjugate and a PEG-peptide conjugate with human renal epithelial cells (HK-2) intermixed into a bio-hybrid hydrogel. The cells are cultured up to the formation of tubule structures. Kidney tubules already formed after four weeks in culture. Throughout the culture period, toxicity and tubulogenesis studies can be performed at any stage of tubule development.

Figure 2A:
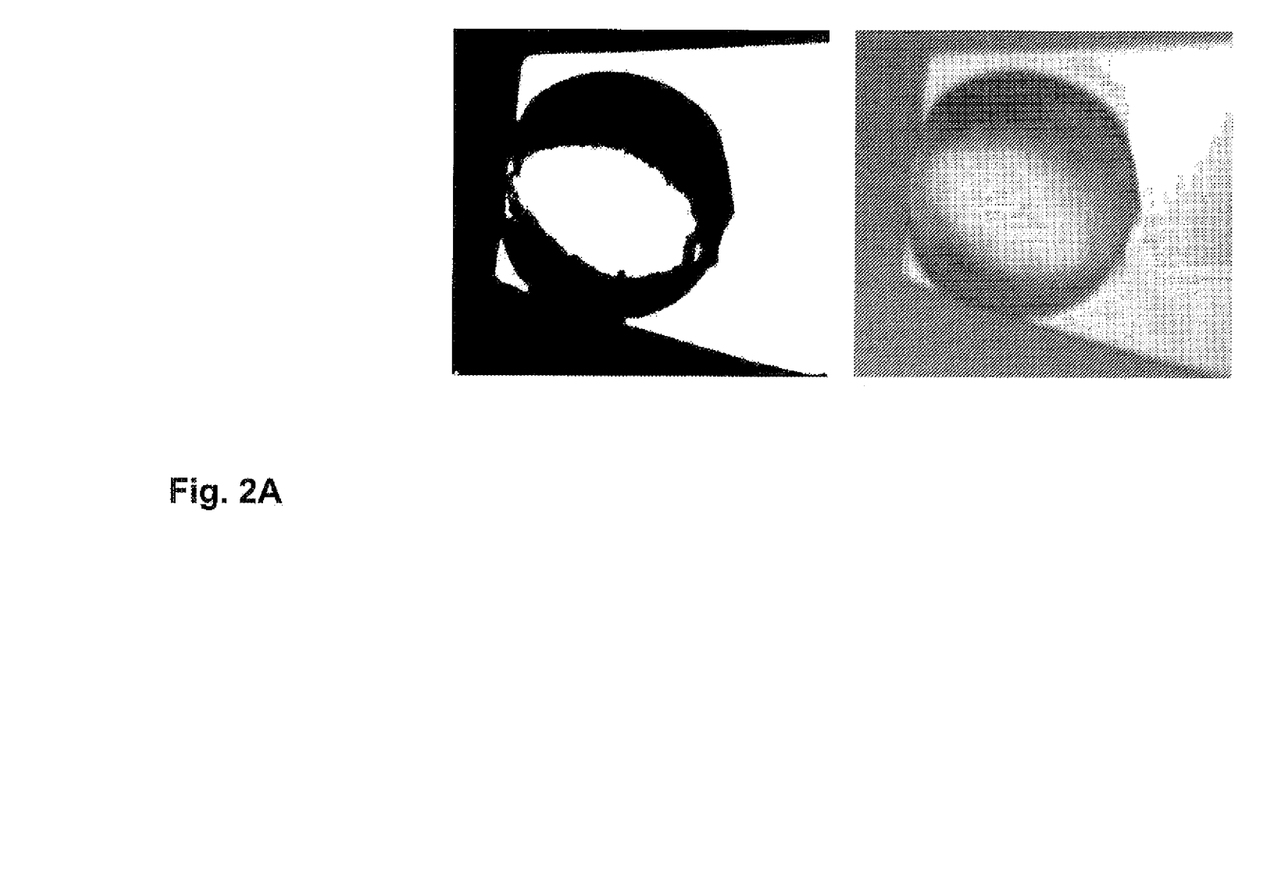
FIG. 2A: a hydrogel with primary proximal cells on a metal spatula after four weeks in the culture.

FIG. 2A shows a hydrogel with primary proximal cells on a metal spatula after four weeks in the culture. The hydrogels, which form stable disks, can then be easily processed.

Figure 2B:
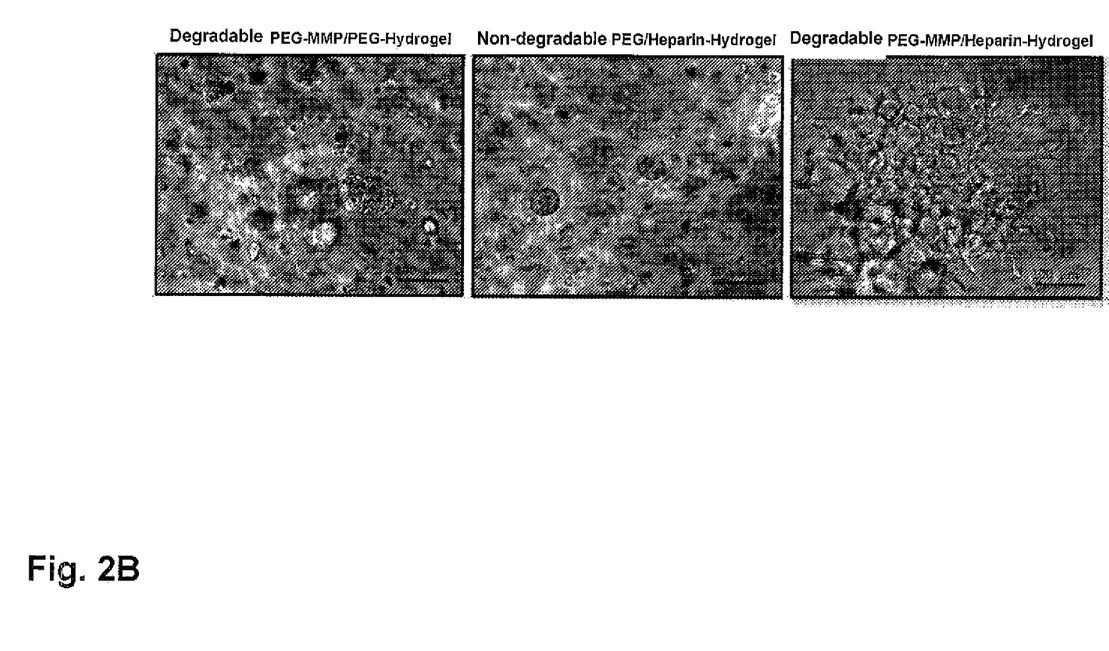
FIG. 2B: micrographs of renal structures after 4 weeks in the culture of HK-2 cells in different hydrogel systems.

Hydrogels may also be produced from heparin with an adapted sulfatization pattern or other glycosaminoglycans such as hyaluronic acid or chondroitin sulfate. FIG. 2B shows micrographs of three different hydrogel systems with HK-2 cells, a degradable PEG-MMP/PEG hydrogel, a non-degradable (non-cleavable) PEG/heparin hydrogel, and a degradable PEG-MMP/heparin hydrogel. The results of the cultivation were compared. The best results for kidney tubule development were achieved in the degradable PEG-MMP/heparin hydrogel.

The mechanical properties of these hydrogels can be easily adjusted by adjusting the mixing ratio of the two material components, i.e. the molar ratio of PEG-MMP to heparin, i.e. the degree of crosslinking. This creates a modular adjustable system in which the mechanical properties (stiffness) of the system during tubulogenesis can be tested. Variations in stiffness from 200 Pa to 6 kPa are possible, as expressed by the dynamic modulus. The dynamic modulus can preferably be determined by way of oscillatory rheometry. In addition, peptides of the extracellular matrix (ECM) can be attached to the PEG or heparin to study their effect on tubulogenesis. The negative charge of heparin can be used to electrostatically bind soluble factors, such as growth factors or cytokines. These factors can then be released over time to simulate the dynamics of the in vivo environment. In this way, the effect of several factors on renal tubulogenesis could be investigated simultaneously.

Studies have been performed with human proximal cell lines and human primary proximal tubule cells. Cells in the degradable PEG-MMP/heparin hydrogels formed tubule structures with anatomical, physiological and functional properties similar to the properties of in vivo human proximal tubules. None of the previously known in vitro methods have been able to generate in vitro human proximal tubules with a diameter similar to the diameter of in vivo human proximal tubules. The structures also show the classical polarization markers and extracellular matrix components that were also found in the in vivo proximal renal tubules.

The advantages of the invention over the above-mentioned prior art are the following:
a human cell system,
tubule structures are in the anatomical size range,
tubule structures are polarized as in vivo,
tubule structures are functional (transport anionic organic molecules, respond to nephrotoxic agents),
longevity—they can be cultured for at least 5 weeks,
adjustability of the material to study the effects of different cell-signaling signals
an optically clear material for cell images and staining
the applicability for personalized medicine using primary human cells of a patient,
no need for animal testing,
hydrogels can be degraded and the cells can be used for quantitative analysis (FACS, PCR, Western Blot, IHC) or re-transplantation,
method can be used as a high-throughput assay
both metabolic activity and the cytotoxicity can be easily quantified.

The key advantage of the system is that the synthetic star-PEG-MMP/heparin hydrogels cleavable at the MMP peptide enable a method for the ex vivo production of a renal tubule. This bio-hybrid hydrogel provides a stable, adjustable system in which the tubulogenesis can be controlled directly for purposes of tissue engineering. Moreover, unlike several of the above-mentioned prior art methods, this method can use human cells and is thus suitable as a direct model for human renal tubulogenesis. For this reason, it offers an excellent alternative to nephrotoxicity studies in animals or to 2D cell culture models. Also, cells of patients can be used with this method for personalized toxicity studies.

In contrast, in many of the above methods known in the art, renal tubule-like structures are produced from animal cells or stem cells or from structures derived from human cells which are orders of magnitude smaller than the human proximal renal tubules and are frequently also inadequately characterized. By using the method of the invention, tubulogenesis can be fully characterized wherein the tubule structures contain polarization labels and components of the extracellular matrix (ECM) found in in vivo proximal tubules. The present method is the first 3D method of forming structures similar to human tubules having diameters in the physiological size range.

Another advantage of the system is that hydrogels can be degraded as needed through addition of collagenase. The tubule cells can then be further analyzed by quantitative methods, such as polymerase chain reaction (PCR) or flow cytometry, such as fluorescence-activated cell sorting (FACS). The tubule cells can then also be used as a source of cells for cell transplantation in a patient.

Figure 3A:
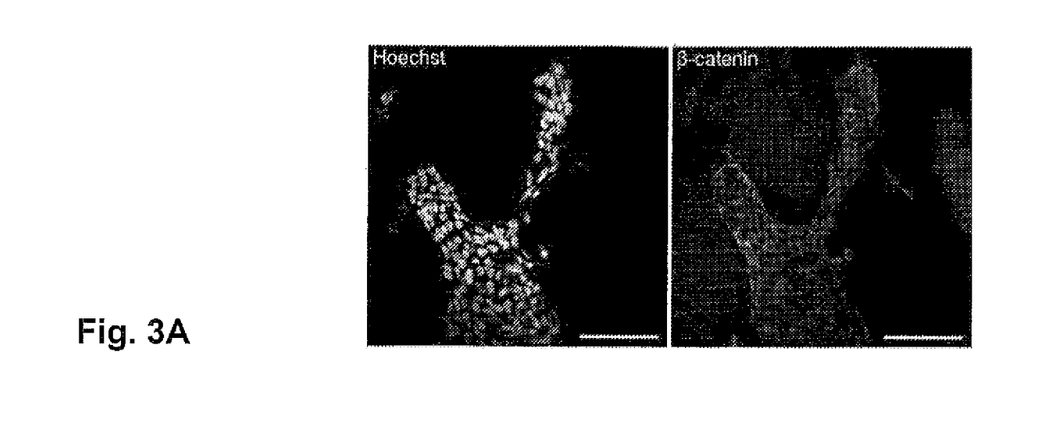
FIG. 3A: micrographs showing the polarization of HK-2 cells after four weeks in the cell culture
Figure 3B:
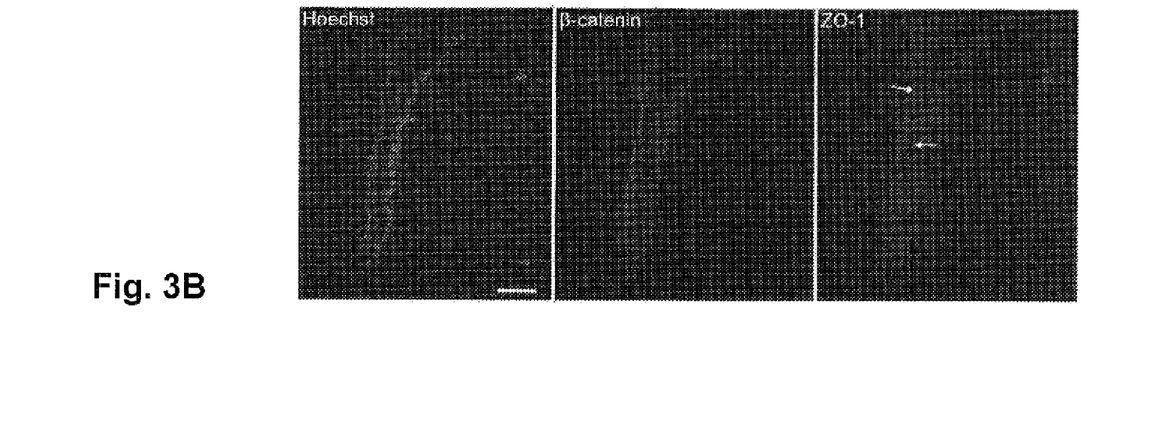
FIG. 3B: micrographs showing immunofluorescence of polarization markers on primary human proximal tubule cells after four weeks in cell culture.

FIG. 3A shows micrographs with a scale bar of 100 μm, showing the polarization of HK2 cells after four weeks in cell culture. FIG. 3B shows micrographs with a scale bar of 100 μm, showing the immunofluorescence of polarization markers on primary human proximal tubule cells after four weeks in cell culture. The arrows indicate the typical close connections between the cells.

Figure 4:
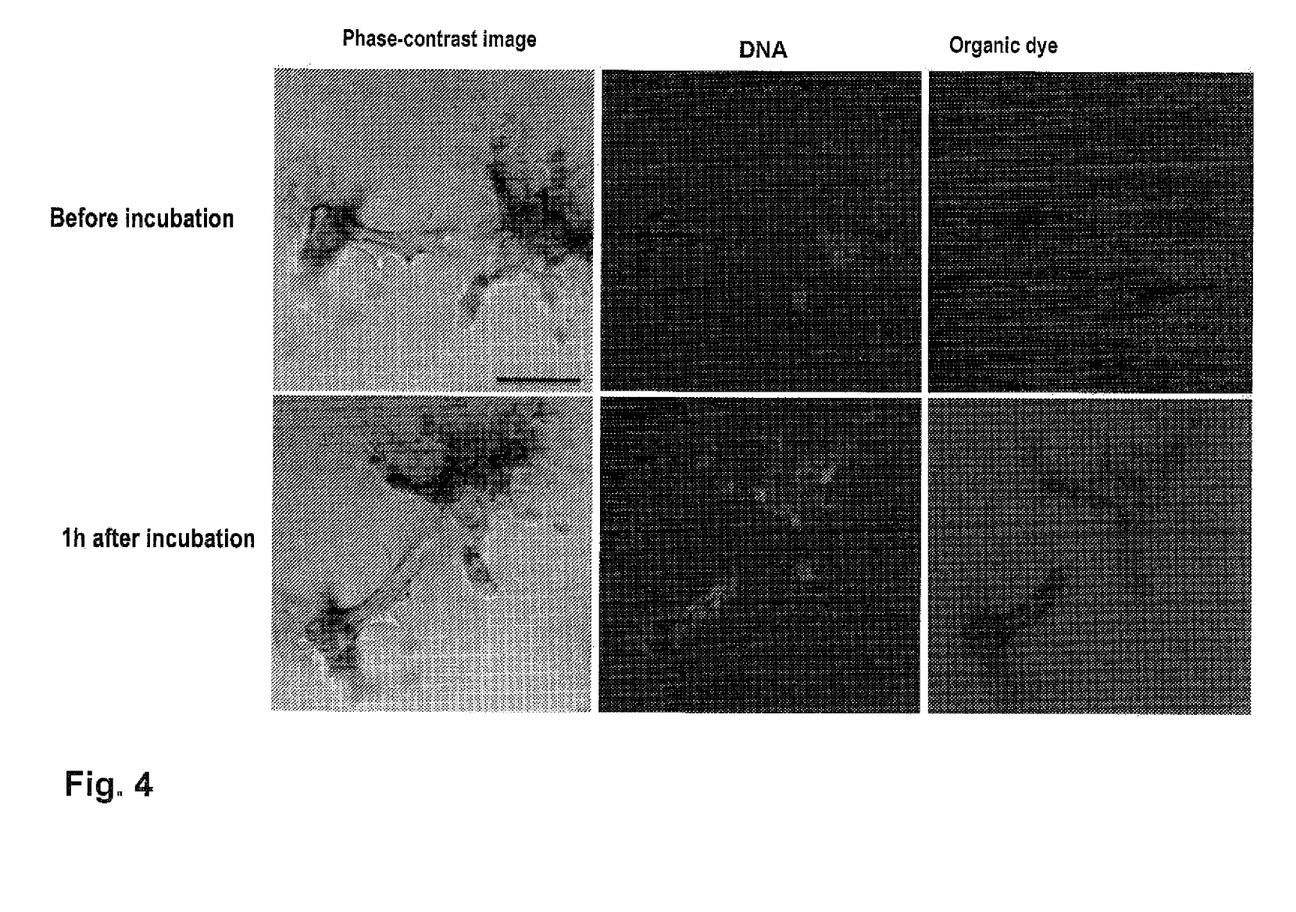
FIG. 4: a micrograph with phase contrast and fluorescent images of the renal tubules in the hydrogel before and after incubation with an anionic, organic fluorescent dye.

FIG. 4 shows a micrograph with a scale bar of 100 μm and phase contrast and fluorescence images of the renal tubules in the hydrogel before (top) and after incubation with an anionic, organic fluorescent dye, in this example the fluorescent organic anionic dye dilithium-4-amino-N-[3-(vinyl sulfonyl)-phenyl]-naphthalimide-3,6-disulfonate, abbreviated as Lucifer Yellow. The functionality of the tubules was demonstrated, inter alia, by the transport function for organic substances. For this purpose, the tubules were cultivated according to the diagram of FIG. 1 (cultivation of the HK-2 cells in the hydrogel) for four weeks in the hydrogel composed of PEG and heparin (with MMP-sensitive peptide linkers) and characterized by light microscopy, i.e. by phase contrast microscopy and confocal laser scanning microscopy, as shown in FIG. 4 before incubation. After characterization by light microscopy, the cell culture medium was removed and replaced with a phenol-red-free medium containing 100 μM of the fluorescent organic anion dye dilithium-6-amino-2-(hydrazincarbonyl)-1,3-dioxo-benzo [de] isoquinoline-5,8-disulfonate referred to as Lucifer Yellow and incubated for one hour. After incubation, the medium was replaced with a dye-free medium and the tubules were re-examined by confocal laser scanning microscopy. The fluorescent dye Lucifer Yellow could now be detected in the lumen of the tubules. Accordingly, the organic anion transporters of the tubules are functionally active. In other words, an important functionality of healthy kidney tubules has been demonstrated, as shown in FIG. 4.

Example 1

The polymeric precursors for hydrogel preparation were composed, as described in Tsurkan et al., Advanced Materials 2013, vol. 25 (18) pp. 2606-2610, of heparin, functionalized with six maleimide groups (HEP-HM6) with a molecular weight of 15,000 g/mol and four-armed PEG functionalized with enzymatically cleavable peptide sequences on each arm with a total molecular weight of 15,500 g/mol (PEG-MMP). The PEG-heparin hydrogels were prepared, as described in Tsurkan et al., Advanced Materials 2013, vol. 25 (18) pp. Described 2606-2610, with the following changes: 50,000 cells (HK-2 cells=human kidney proximal tubule epithelial cells (ATCC CRL-2190)) were dissolved in 12.5 μl HEP-HM6 (0.56 mg HEP-HM6 dissolved in 12.5 μl) which is dissolved in a phosphate buffered saline solution (PBS) and then mixed with 12.5 μl PEG-MMP (0.58 mg PEG-MMP dissolved in 12.5 μl), dissolved in PBS, intermixed to start the gelation. The solids content was 4.4%, the molar ratio of the gel components was 1:1. The cells embedded in hydrogel were cultured for four weeks in DMEM/F-12 medium (Gibco) which was supplemented with 10% fetal bovine serum (FBS, Biochrom) and 1% penicillin/streptomycin. The medium was changed immediately after gelation and every three days thereafter. Surprisingly, tubules were formed from the third week on, and were characterized by light microscopy, see FIG. 2B (right) and FIG. 3A. The resulting hydrogels had a dynamic modulus in the range of 550±250 Pa after gel formation. The dynamic modulus was determined by oscillatory rheometry of hydrogel slices that were swollen in PBS at room temperature by using a rotational rheometer (ARES LN2, TA Instruments, Eschborn, Germany) with a plate-plate measuring device with a plate diameter of 25 mm by frequency-dependent measurement at 25° C. in a shear frequency range $10^{-1}$-$10^{2}$ rad $s^{-1}$ with a deformation amplitude of 2%.

Example 2

Figure 5:
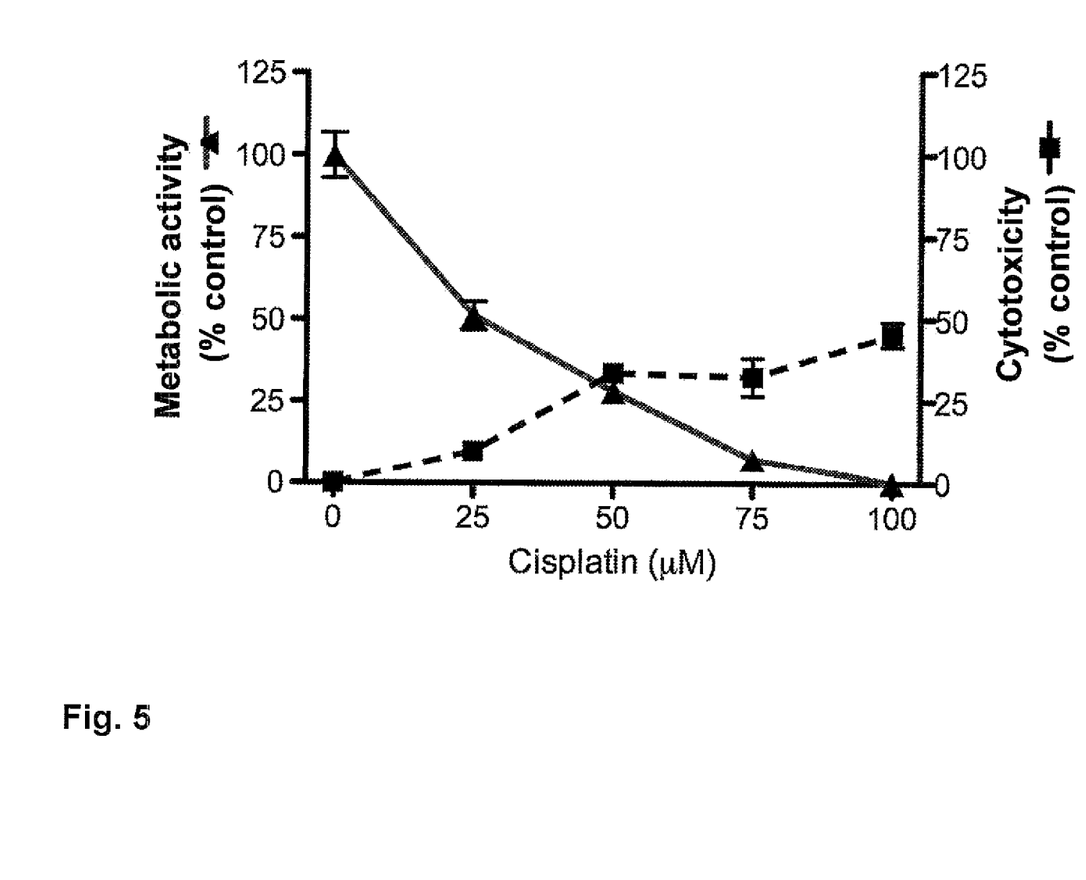
FIG. 5: a diagram showing the metabolic activity and cytotoxicity after 48 hours incubation with cisplatin using HK-2 cells.
Figure 6:
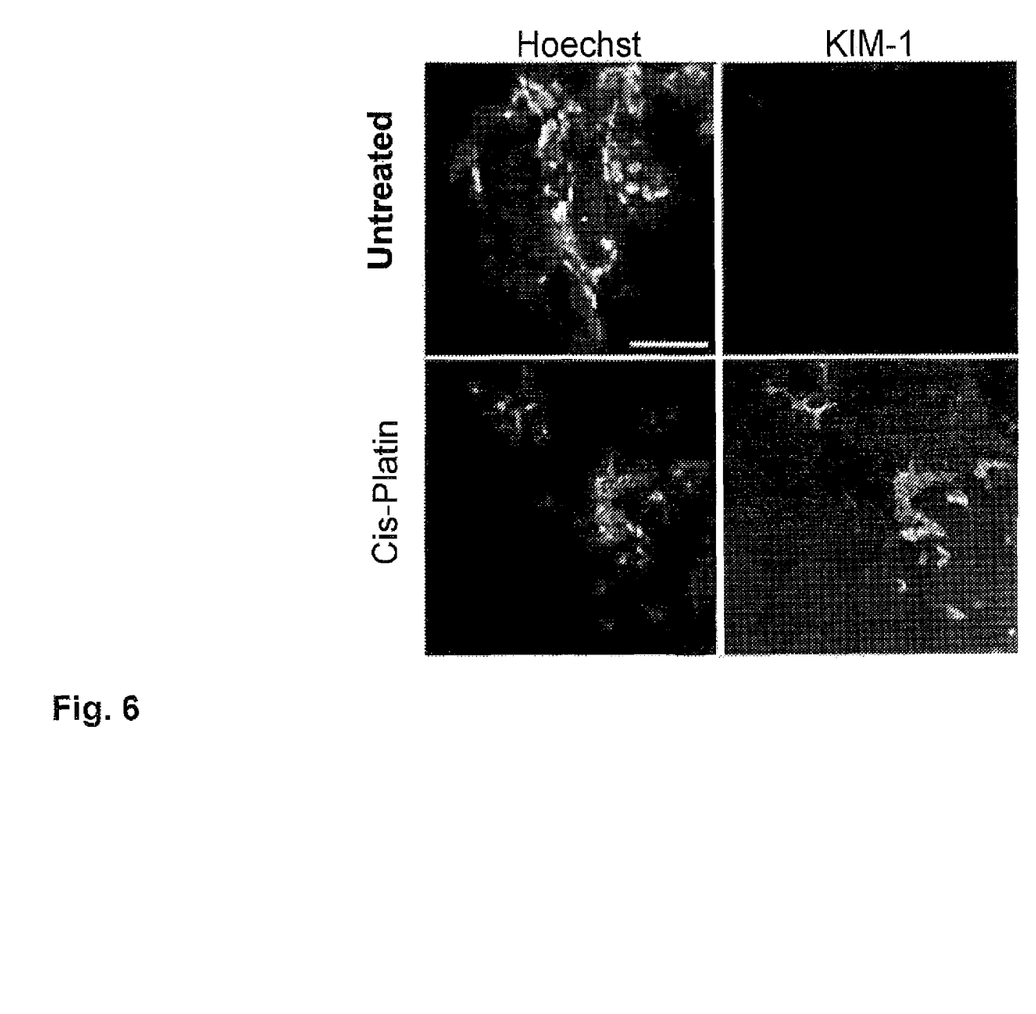
FIG. 6: micrographs showing the expression of a kidney damage biomarker, KIM-1, after incubation with or without cisplatin, using HK-2 cells.

The present invention can be used as an assay for nephrotoxicity. This was demonstrated by incubating the tubule structures with the nephrotoxic chemotherapeutic agent cisplatin. Cisplatin uptake from renal tubule cells activates signaling pathways that promote cell death and increase the production of pro-inflammatory cytokines that also contribute to injury and cell death. After four weeks in the culture, in analogy to Example 1 with HK-2 cells, the tubule organoids were incubated for 48 hours with a serum-free medium containing 0 to 100 μM cisplatin. After incubation with the active ingredient, metabolic activity decreased depending on the dose, as shown in FIG. 5. Conversely, the cytotoxicity of the tubules increased with increasing cisplatin dosage, as also shown in FIG. 5. Cisplatin also causes an increase in apoptosis, meaning cell death, which could be observed with caspase-3 immunocytochemistry. As shown in FIG. 6, the injured structures also expressed the injury-indicating kidney biomarker KIM 1, which is also used in vivo to characterize injured kidney structures.

Example 3

The method of Example 2 may also be repeated with other active ingredients, such as doxorubicin or toxins such as lipopolysaccharides, in order to model sepsis. The tubule structures can be incubated with the active ingredient doxorubicin, with a content of 0 to 100 μM. For the metabolic and cytotoxicity measurements, similar results can be expected as in FIG. 5. Thus, cell death and the KIM-1 expression may hence also be analyzed.

Example 4

Figure 7:
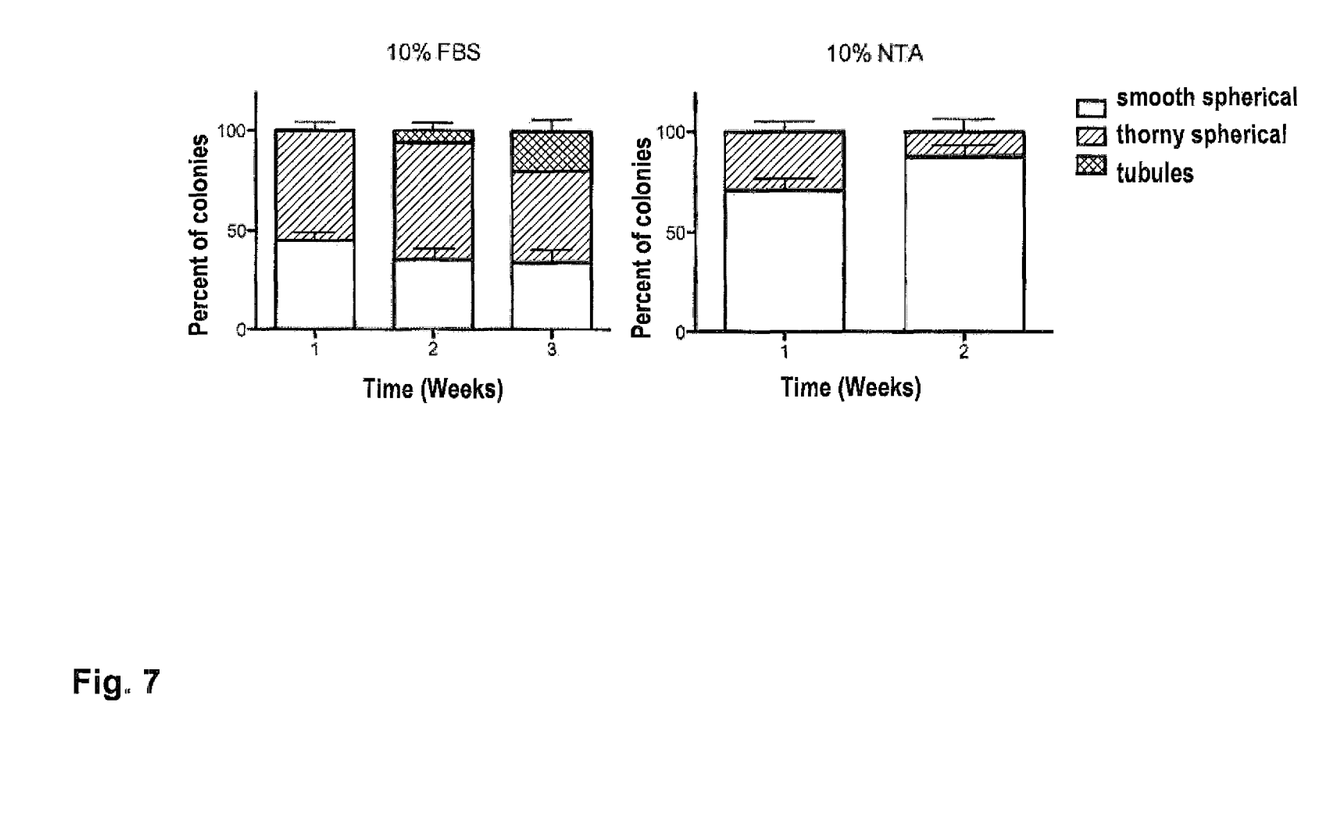
FIG. 7: a diagram comparing the quantification of tubulogenesis using HK-2 cells with 10% fetal bovine serum (FBS) and 10% pannexine NTA serum replacement (NTA)
Figure 8:
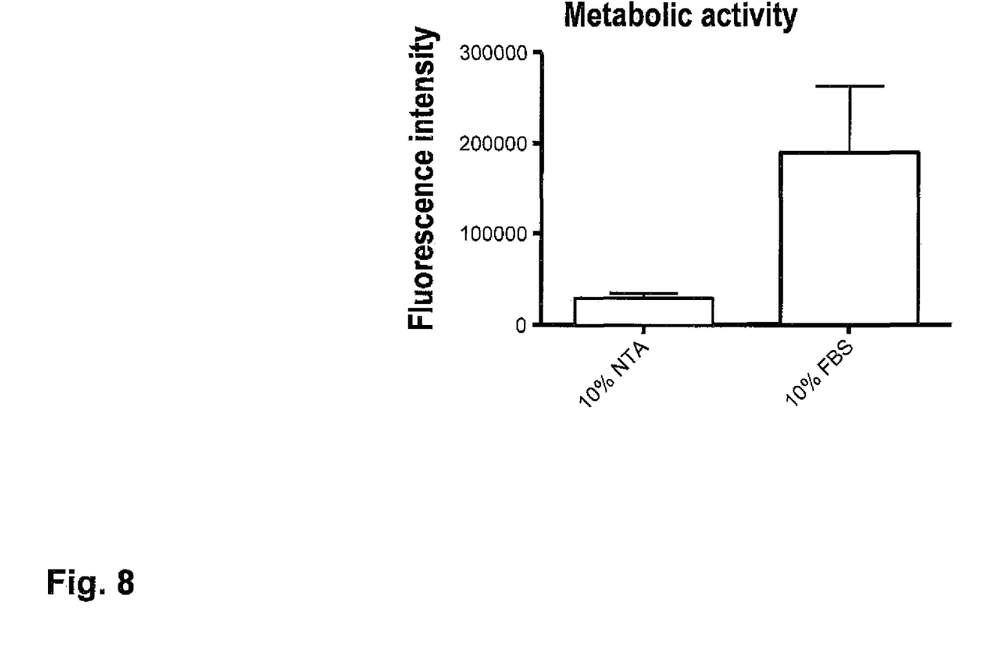
FIG. 8: a comparison of the metabolic activity of the culture of HK-2 cells with fetal bovine serum (FBS) and of the culture with 10% pannexine NTA serum replacement (NTA), measured with a Presto Blue-assay in the third week of the cell culture.

The model can also be used to study how growth factors promote kidney tubulogenesis. In this example, the effect of growth factors in the serum was investigated. Panexin NTA from the company PAN-Biotech, a serum replacement containing no growth factors, was added to the medium in the same concentration as the reference serum (control), 10% fetal bovine serum (FBS). The tubulogenesis was quantified over the duration of the culture and the metabolic activity was measured after three weeks in the culture. As shown in FIG. 7, the lack of growth factors in the serum inhibits tubulogenesis. The metabolic activity of the cells was also increased by the addition of 10% FBS, as shown in FIG. 8.

What is claimed is:

1. A method for forming renal tubules comprising
embedding individual human kidney cells in a synthetic three-dimensional hydrogel matrix, wherein said synthetic three-dimensional hydrogel matrix comprising polyethylene glycol as a component, said polyethylene glycol molecules are crosslinked via peptides with molecules of heparin, hyaluronic acid or chondroitin sulfate and the synthetic three-dimensional matrix is intermixed with the human kidney cells, wherein the peptides are enzymatically cleavable to allow for cell-controlled degradation and reconfiguration of the hydrogel matrix; and
continually culturing the hydrogel embedded cells in a culture medium comprising a serum containing growth factors until tubule structures are formed to a size, structure, morphology and functionality corresponding to or resembling human renal tubules.

2. The method according to claim 1, wherein the individual human kidney cells are derived from cells of the group consisting of kidney tubule cell lines, primary renal tubule cells, cells derived from Induced pluripotent stem cells (iPSCs) and mesenchymal stem cells.

3. The method according to claim 2 wherein the human primary renal tubule cells are proximal tubule cells, distal tubule cells or collecting tubule cells.

4. The method according to claim 2, wherein one of the renal tubule cell lines is an immortalized proximal tubular epithelial cell line derived from normal adult human kidney tissue.

5. The method according to claim 1, wherein the functionality of the renal tubules Is determined by one or more cellular events of the group consisting of expression of human renal markers, a response to known nephrotoxic compounds, a resulting expression of renal Injury and apoptosis markers, and an ability of the tubules to transport anionic charged organic molecules into a lumen of the tubules.

6. The method according to claim 2 wherein the tubule cells are co-cultivated together with mesenchymal stem cells and/or kidney cells and/or endothelial cells, which are co-localized with the tubule cells in the hydrogel.

7. The method according to claim 6, wherein the tubule cells are co-cultivated together with human mesenchymal stem cells and/or human kidney cells and/or human endothelial cells, which are co-localized with the tubule cells in the hydrogel.

8. The method according to claim 1, wherein the cleavable peptides are matrix metalloproteinase-cleavable peptides.

\* \* \* \* \*